| United States Patent [19] | [11] Patent Number: 4,885,426 |
|---|---|
| Chu et al. | [45] Date of Patent: Dec. 5, 1989 |

[54] TRANSALKYLATION OF POLYAROMATICS

[75] Inventors: Yung F. Chu, Plainsboro; David O. Marler, Deptford; John P. McWilliams, Woodbury, all of N.J.

[73] Assignee: Mobil Oil Corporation, New York, N.Y.

[21] Appl. No.: 327,378

[22] Filed: Mar. 23, 1989

Related U.S. Application Data

[63] Continuation of Ser. No. 92,503, Sep. 2, 1987, abandoned.

[51] Int. Cl.$^4$ ................................................ C07C 5/22
[52] U.S. Cl. ...................................... 585/474; 585/475
[58] Field of Search ................................. 585/474, 475

[56] References Cited

U.S. PATENT DOCUMENTS

| Re. 27,639 | 5/1973 | Thomas et al. | 260/672 T |
|---|---|---|---|
| 2,904,607 | 9/1959 | Mattox et al. | 260/671 |
| 3,251,897 | 5/1966 | Wise | 260/671 |
| 3,551,509 | 12/1970 | Thomas et al. | 260/672 |
| 3,751,504 | 8/1973 | Keown et al. | 585/474 |
| 3,751,506 | 8/1973 | Burress | 260/671 R |
| 3,945,913 | 3/1976 | Brennan et al. | 208/137 |
| 3,962,364 | 6/1976 | Young | 260/671 C |
| 4,016,218 | 4/1977 | Haag et al. | 260/671 R |
| 4,127,616 | 4/1978 | Rodeweld | 585/475 |
| 4,169,111 | 9/1979 | Wight | 585/323 |
| 4,361,713 | 11/1982 | Kaeding | 585/467 |
| 4,365,104 | 12/1982 | Kaeding | 585/467 |
| 4,367,359 | 1/1983 | Kaeding | 585/467 |
| 4,370,508 | 1/1983 | Kaeding | 585/467 |
| 4,380,685 | 4/1983 | Chu | 585/466 |
| 4,384,155 | 5/1983 | Chu | 585/466 |
| 4,418,235 | 11/1983 | Haag et al. | 585/474 |
| 4,547,605 | 10/1985 | Kresge et al. | 585/467 |
| 4,599,475 | 7/1986 | Kresge et al. | 585/481 |
| 4,694,114 | 9/1987 | Chu et al. | 585/481 |

FOREIGN PATENT DOCUMENTS 0141514  5/1985  European Pat. Off. .

*Primary Examiner*—Curtis R. Davis
*Attorney, Agent, or Firm*—Alexander J. McKillop; Charles J. Speciale; Marina V. Schneller

[57] ABSTRACT

A process is provided for transalkylation of polyalkylaromatics over a catalyst comprising a molecular sieve having a high lattice aluminum content whereby its silica/alumina mole ratio is less than 40 and an alpha value of at least about 140.

13 Claims, No Drawings

TRANSALKYLATION OF POLYAROMATICS

This is a continuation of copending application Ser. No. 092,503, filed on Sept. 2, 1987, and now abandoned.

This invention is directed to a process for transalkylating a polyaromatic hydrocarbon charge to prepare monoalkylaromatics in the presence of catalyst comprising a crystalline molecular sieve characterized by a silica/alumina mole ratio less than about 40, a Constraint Index of from about 1 to about 12 and having an alpha value of at least about 140.

Zeolitic materials, both natural and synthetic, have been demonstrated in the past to have catalytic properties for various types of hydrocarbon conversions. Certain zeolitic materials are ordered, porous crystalline molecular sieves having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Prior art techniques have resulted in the formation of a great variety of synthetic molecular sieves. These materials have come to be designated by convenient symbols, as illustrated by ZSM-5 (U.S. Pat. No. 3,702,886).

The use of certain molecular sieves as catalyst components is taught in U.S. Pat. No. 4,305,808, for example.

The silica/alumina molar ratio of a given molecular sieve is often variable; for example, zeolite X (U.S. Pat. No. 2,882,244) can be synthesized with a silica/alumina ratio of from 2 to 3; zeolite Y (U.S. Pat. No. 3,130,007) from 3 to about 6. In some molecular sieves, the upper limit of silica/alumina ratio is virtually unbounded. ZSM-5 is one such material wherein the silica/alumina ratio is at least 5. U.S. Pat. No. 3,941,871 (Re. 29,948) discloses a porous crystalline silicate made from a reaction mixture containing no deliberately added alumina and exhibiting an X-ray diffraction pattern characteristic of ZSM-5. U.S. Pat. Nos. 4,061,724; 4,073,865 and 4,104,294 describe crystalline silicates of varying alumina and metal content.

It is known that zeolites are stabilized for various processes by reducing lattice aluminum content. In FCC applications, for example, the catalyst of choice is ultrastable Y which has been dealuminized from its precursor Y form by steaming. Another example of stability enhancement by catalyst dealuminization is in hydrodewaxing. U.S. Pat. No. 4,247,388 teaches the improvement of catalyst aging characteristics in lube dewaxing by steaming ZSM-5 to reduce lattice aluminum content.

U.S. Pat. No. 4,380,685 teaches para-selective alkylation, transalkylation or disproportionation of a substituted aromatic compound to form a dialkylbenzene compound mixture over catalyst comprising zeolite characterized by a Constraint Index of 1 to 12 and a silica/alumina mole ratio of at least 12/1, the catalyst having thereon incorporated various metals and phosphorus. Other patents covering alkylation and transalkylation include U.S. Pat. Nos. 4,127,616; 4,361,713; 4,365,104; 4,367,359; 4,370,508 and 4,384,155. Alkylation with olefins is taught, for example, in U.S. Pat. Nos. 3,962,364 and 4,106,218.

U.S. Pat. Nos. 3,551,509 and Re. 27,639 disclose transalkylation between trimethylbenzenes and toluene to yield xylenes and benzene in the presence of a crystalline aluminosilicate catalyst having large pore openings of 8 to 15 Angstrom units and, preferably containing Group VIII metals, hydrogen and rare earth cations.

Alkylation of aromatic hydrocarbons utilizing porous crystalline silicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes liquid phase alkylation in the presence of X- or Y-type crystalline aluminosilicate zeolite, specifically such type zeolites wherein the cation is rare earth and/or hydrogen. U.S. Pat. No. 3,751,504 to Keown et al., and U.S. Pat. No. 3,751,506 to Burress describe vapor phase alkylation of aromatic hydrocarbons with olefins, e.g., benzene with ethylene, in the presence of a ZSM-5 zeolite catalyst. U.S. Pat. No. 4,016,218 to Wise describes vapor phase alkylation with a shape-selective zeolite such as ZSM-5 which has been modified by steaming to an alpha value less than 250. U.S. Pat. No. 4,169,111 to Wight describes alkylation of benzene with ethylene wherein polyethylbenzene by-products are subjected to transalkylation with benzene in a separate transalkylation zone to produce ethylbenzene using a ZSM-5 catalyst having a $SiO_2/Al_2O_3$ ratio of between 2 and 80. All of the above patents are incorporated herein by reference.

During the alkylation of alkylatable aromatic compounds, undesirable polyalkylaromatics can be formed which can be recycled to the alkylation reactor where further conversion to monoalkylaromatics can occur. However, polyalkylaromatics can cause the formation of heavy aromatic residues and enhance catalyst aging in the alkylation reactor. Accordingly, polyalkylaromatics can be removed to a separate transalkylation reactor having the same reactor conditions and catalyst as the alkylation reactor, as is taught by U.S. Pat. No. 3,751,504 to Keown et al. This reference teaches the use of ZSM-5 having a $SiO_2/Al_2O_3$ molar ratio of 5 to 300, preferably 5 to 100.

U.S. application Ser. No. 092,504, filed Sept. 2, 1987, filed contemporaneously with the present application relates to a method for alkylating an aromatic hydrocarbon charge whereby o-xylene production is minimized utilizing a catalyst similar to but of lower activity than the catalyst employed in the present invention.

U.S. application Ser. No. 092,842, filed Sept. 2, 1987, filed contemporaneously with the present application, relates to a vapor phase disproportionation of toluene, utilizing catalysts similar to those employed in the present invention.

U.S. application Ser. No. 014,147, filed Feb. 12, 1987 relates to a method for preparing zeolites from a non-organic reaction mixture, having a low silica to alumina molar ratio such as those used in the present invention.

It has now been found that transalkylation is preferably carried out under conditions dissimilar to those employed during alkylation. In particular, it has been found that transalkylation is thermodynamically favored at lower temperatures while using catalysts of higher acid activity than those employed in alkylation. In particular, it has been found that higher acidity zeolites are capable of greater benzene retention, evidencing increased selectivity toward monoalkylaromatic product. Greater benzene retention reduces the amount of benzene required for transalkylation, permitting more economical operation.

This invention contemplates a process for effecting transalkylation of polyalkylaromatics which comprises contacting a polyalkylaromatic hydrocarbon charge with benzene under conditions effective for accomplishing said transalkylation, including a reactor inlet temperature between about 400° F. and about 1,000° F., preferably between about 500 and about 850° F., a pressure between about 0 and about 3000 psig, preferably between about 25 and 750 psig, a total feed weight hourly space velocity (WHSV) between about 0.1 hr$^{-1}$ and about 100 hr$^{-1}$, preferably between about 2 and 50 hr$^{-1}$, and a hydrogen to hydrocarbon mole ratio of from about 0 to about 4, preferably from about 0 to about 2, with a catalyst composition comprising a crystalline molecular sieve having a high lattice aluminum content characterized by a silica/alumina mole ratio of less than 40, preferably from about 20 to about 30, a Constraint Index of from about 1 to about 12 and an alpha value greater than about 140, preferably at least about 200. The above WHSV is based upon the weight of catalyst molecular sieve, i.e. total weight of active catalyst component.

The present invention relates to a transalkylation process for polyalkylaromatics. U.S. Pat. No. 4,169,111, incorporated herein by reference in its entirety, is illustrative of a prior art process for transalkylation of polyalkylaromatics over a wide range of conditions and with a catalyst composition comprising a crystalline molecular sieve characterized by a silica/alumina mole ratio of between 2 and 80, e.g., X, Y, L, B, ZSM-5 and Omega Crystal types.

For the present improved process, the catalyst will comprise a crystalline molecular sieve material having a structure which will permit a Constraint Index of from about 1 to about 12. The silica/alumina mole ratio of the molecular sieve for use herein, however, will be less than 40, preferably from about 20 to less than 30, e.g. from about 20 to about 28. The alpha value of the catalyst employed in the presently claimed process should be at least about 140, preferably about 200 to about 3500 or even more preferably from about 500 to about 3000. A definition of alpha value and technique employed in its determination are given below.

The crystalline molecular sieves which can be made to exhibit the above required properties include those having the structure of ZSM-5, ZSM-11, ZSM-5/ZSM-11 intermediate, ZSM-12, ZSM-22, ZSM-23, ZSM-35, ZSM-38, ZSM-48, ZSM-50 and Beta with ZSM-5 and ZSM-11 particularly preferred. ZSM-5 is described in U.S. Pat. No. 3,702,886, the contents of which are incorporated herein by reference. ZSM-11 is described in U.S. Pat. No. 3,709,979, the contents of which are incorporated herein by reference. ZSM-5/ZSM-11 intermediate is described in U.S. Pat. No. 4,229,424, the contents of which are incorporated herein by reference. ZSM-12 is described in U.S. Pat. No. 3,832,449, the contents of which are incorporated herein by reference. ZSM-23 is described in U.S. Pat. No. 4,076,842, the contents of which are incorporated herein by reference. ZSM-35 is described in U.S. Pat. No. 4,016,245, the contents of which are incorporated herein by reference. ZSM-38 is described in U.S. Pat. No. 4,046,859, the contents of which are incorporated herein by reference.

ZSM-48 is described in U.S. Pat. No. 4,397,827, the contents of which are incorporated herein by reference. ZSM-50 is described in U.S. Pat. No. 4,640,849, the contents of which are incorporated herein by reference. Beta is described in U.S. Pat. No. 3,308,069, the contents of which are incorporated herein by reference.

ZSM-22 is a molecular sieve which can be made to be useful in the present improved process. In general, its as-synthesized composition is as follows:

$$(x)Q_2O:(y)M_{2/n}O:(z)Al_2O_3:100SiO_2$$

wherein $Q_2O$ is the oxide form of an organic compound containing an element of Group VA of the Periodic Table of the Elements, e.g. N or P, preferably N, containing at least one alkyl or aryl group having at least 2 carbon atoms, M is an alkali metal or an alkaline earth metal having a valence n, and $x = 0.01-2.0$, $y = 0-2.0$ and $z = 0-5$.

ZSM-22 has a definite X-ray diffraction pattern, set forth below in Table I, which distinguishes it from other crystalline materials.

TABLE I

| Interplanar d-spacings (A) | Relative Intensity (I/Io) |
|---|---|
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 I/$I_o$ is the intensity of the strongest line or peak, and d (obs.) the interplanar spacing in Angstroms (A), corresponding to the recorded liens, were determined. In Table I, the relative intensities are given in terms of the symbols VS = very strong, M = medium, W = weak, etc. It should be understood that this X-ray diffraction pattern is characteristic of all the species of ZSM-22. Ion exchange of the alkali metal cations with other ions results in substantially the same X-ray diffraction pattern with some minor shifts in interplanar spacing and variation in relative intensity. Other minor variations can occur, depending on the silica/alumina ratio of the particular sample, as well as its degree of thermal treatment.

ZSM-22 can be suitably prepared from a reaction mixture containing a source of silica, an alkane diamine, an alkali metal oxide or an alkaline earth metal oxide (e.g. sodium, potassium, cesium, calcium or strontium), water, and alumina, and having a composition, in terms of mole ratios of oxides, within the following ratios:

| Reactants | Broad | Preferred |
|---|---|---|
| $SiO_2/Al_2O_3 =$ | 20 or more | 30 to 1000 |
| $H_2O/SiO_2)_2 =$ | 10 to 100 | 20 to 60 |

| Reactants | Broad | Preferred |
| --- | --- | --- |
| $OH^-/SiO_2 =$ | 0 to 0.3 | 0.1 to 0.2 |
| $M^+/SiO_2 =$ | 0 to 2.0 | 0.1 to 1.0 |
| $RN/SiO_2 =$ | 0.01 to 2.0 | 0.05 to 1.0 | wherein RN is a $C_2$-$C_{12}$ alkane diamine of the formula $H_2N$—$(CH_2)_n$—$NH_2$ (abbreviated $C_nDN$), n=2 to 12, and preferably is 5 to 8, and M is an alkali metal or an alkaline earth metal, and maintaining the mixture at crystallization temperature until crystals of ZSM-22 are formed. Thereafter, the crystals are separated from the liquid by a conventional means, washed and recovered.

The original cations of the above molecular sieves are preferably replaced in accordance with techniques well known in the art, at least in part, with hydrogen or hydrogen precursor cations and/or non-noble metal ions of Group VIII of the Periodic Table, e.g. nickel, iron and/or cobalt.

The member of the class of molecular sieves useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structures may exist which may be operative for other reasons, and therefore, it is not the present intention to entirely judge the usefulness of the particular molecular sieve solely from theoretical structure considerations.

A convenient measure of the extent to which a crystal provides access to molecules of varying sizes to its internal structure is the Constraint Index of the crystal. Crystalline materials which provide a highly restricted access to and egress from its internal structure have a high value for the Constraint Index, and materials of this kind usually have pores of small size, e.g. less than 5 Angstroms. On the other hand, crystalline materials which provide relatively free access to the internal crystal structure have a low value for the Constraint Index, and usually pores of large size, e.g. greater than 8 Angstroms. The method by which Constraint Index is determined is described fully in U.S. Pat. No. 4,106,218 incorporated herein by reference.

Constraint Index (CI) values for some typical materials are:

| | CI (at test temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those molecular sieves which are useful in the instant invention. The very nature of this parameter and the recited technique by which it is determined, however, admit of the possibility that a given material can be tested under somewhat different conditions and thereby exhibit different Constraint Indices. Constraint Index seems to vary somewhat with severity of operations (conversion) and the presence or absence of binders. Likewise, other variables, such as crystal size, the presence of occluded contaminants, etc., may affect the Constraint Index. Therefore, it will be appreciated that it may be possible to so select test conditions, e.g. temperature, as to establish more than one value for the Constraint Index of a particular crystalline material. This explains the range of Constraint Indices for some molecular sieves, such as ZSM-5, ZSM-11 and Beta.

It is to be realized that the above CI values typically characterize the specified crystalline materials, but that such are the cumulative result of several variables useful in the determination and calculation thereof. Thus, for a given crystal exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the material, the presence of possibly occluded contaminants and binders intimately combined with the crystal may affect the CI. It will accordingly be understood to those skilled in the art that the CI, as utilized herein, while affording a highly useful means for characterizing the molecular sieves of interest is approximate, taking into consideration the manner of its determination, with the possibility, in some instances, of compounding variable extremes. However, in all instances, at a temperature within the above-specified range of 290° C. to about 538° C., the CI will have a value for any given molecular sieve of interest herein within the approximate range of 1 to 12.

The molecular sieve for use herein or the catalyst comprising same can be thermally treated at high temperatures. This thermal treatment is generally performed by heating at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

For the transalkylation process of this invention the suitable molecular sieve may be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline molecular sieve of the total composition of catalyst and binder or support may vary widely with the zeolite content ranging from between about 30 to about 90 percent by weight and more usually in the range of about 50 to about 80 percent by weight of the composition. The composition may be in the form of an extrudate, beads or fluidizable microspheres.

Operating conditions employed in the process of the present invention are critical. Such conditions as temperature, pressure, space velocity, molar ratio of the reactants and hydrogen to hydrocarbon mole ratio will have important effects on the process.

The process of this invention is conducted such that alkylation of polyalkylaromatics is carried out by contact in a reaction zone, such as, for example, a fixed bed of catalyst composition, under transalkylation effective conditions, said catalyst composition being characterized as comprising the above-defined molecular sieve, preferably which has been hydrogen, or hydrogen precursor exchanged and/or thermally treated. The effluent is separated and distilled to remove desired product, such as monoalkylaromatics, and unreacted reactants, benzene and polyalkylaromatics are recycled for further reaction.

By the present improved process polyalkylaromatics such as triethylbenzene and diethylbenzene can be converted to aromatic concentrates of high value, e.g. ethylbenzene. This process may be conducted in either batch or fluid bed operation with attendant benefits of either operation readily obtainable.

Typical feedstocks are those containing 40 to 80 wt % benzene, 15 to 50 wt. % dialkylbenzene, and 2 to 20 wt. % $C_9$ monoalkylaromatics and 0 to 5 wt. % $C_9$ aromatics. The following specific examples will serve to illustrate the process of the present invention, without unduly limiting same. In the examples, when Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec $^{-1}$). The Alpha Test is described in U.S. Pat. No. 3,354,078 and in *The Journal of Catalysis*, Vol. IV, pp. 522-529 (August 1965), each incorporated herein as to that description. It is noted that intrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589-591, 14 June 1984).

EXAMPLE 1

Three separate molecular sieves were prepared for testing of the present concept and comparisons to determine important process/catalyst limitations.

MOLECULAR SIEVE A

For the synthesis of the crystals a 7.3 parts quantity by weight of water was mixed with 12.8 parts, 50% NaOH, 10.1 parts $Al_2(SO_4)_3 14H_2O$, 1.6 parts ZSM-5 seeds and 68.2 parts amorphous silica (047.6% solids) prepared by the neutralization of sodium silicate with sulfuric acid. The reaction mixture had a composition in mole ratios of:

| $SiO_2/Al_2$ | 32 |
| --- | --- |
| $H_2O/SiO_2$ | 5.45 |
| $OH^-/SiO_2$ | 0.105 |
| $OH^-/H_2O$ | 0.0192 |

The reaction mixture was heated directly to 220° F. and stirred in an autoclave at that temperature for crystallization. After full crystallinity was achieved, the resulting crystals were separated from remaining liquid by filtration, washed with water and dried.

MOLECULAR SIEVE B

A 15.0 parts quantity by weight of water was mixed with 11.0 parts 50% NaOH, 9.0 parts $Al_2(SO_4)_3 .14 H_2O$ and 65.0 parts amorphous silica (42.7% solids) prepared by the neutralization of sodium silicate with sulfuric acid. The reaction mixture had a composition in mole ratios of:

| $SiO_2/Al_2O_3$ | 32 |
| --- | --- |
| $H_2O/SiO_2$ | 7.04 |
| $OH^-/SiO_2$ | 0.104 |
| $OH^-/H_2O$ | 0.015 |

The reaction mixture was then heated to 350° F. and stirred in an autoclave at that temperature for crystallization. After full crystallinity was achieved, the resulting crystals were separated from remaining liquid by filtration, washed with water and dried.

The crystals were then formed into an extrudate containing 35 weight percent alumina. The extrudate was exchanged w/NaCl, steamed at 0 psig and 100% steam at 700° F. for 6 h, and then calcined at 1000° F. for 3 h in air.

MOLECULAR SIEVE C

A 1.4 parts quantity by weight of tripropylamine was added to a mixture containing 2.1 parts n-propylbromide, 4.0 parts methylethylketone, 6.9 parts sodium chloride, 0.1 part dispersant (mixture of polymerized aryl and substituted benzoid alkyl sulfonic acids), 3.2 parts 93% $H_2SO_4$, 1.3 parts $Al_2(SO_4)_3 .14 H_2O$, 37 percent sodium silicate (28.5% $SiO_2$, 8.8% $Na_2O$) and 43 parts water. The reaction mixture had a composition of the following molar ratios:

| $SiO_2/Al_2O_3$ | 78 |
| --- | --- |
| $H_2O/SiO_2$ | 21.09 |
| $OH^-/SiO_2$ | 0.087 |
| $N/Al_2O_3$ | 7.57 | where N is tripropylamine and the hydroxide concentration is based only on inorganic sources.

The reaction mixture was then heated directly to 220° F. and stirred in an autoclave at that temperature for crystallization. After full crystallinity was achieved, the resulting crystals were separated from the remaining liquid by filtration, washed with water and dried.

The above molecular sieve materials were evaluated for composition, e.g. alumina, silica and sodium contents, surface area, particle density, pore volume and Alpha Value. All had sodium contents of less than 500 ppm. Other results of these evaluations are listed in Table II below.

TABLE II

| Molecular Sieve | A | B | C |
|---|---|---|---|
| $SiO_2/Al_2O_3$, mole ratio | 25 | 25* | 70 |
| Surface area, $m^2/g$ | 333 | 325 | — |
| Particle density, g/cc | 1.01 | 0.95 | — |
| Pore volume, cc/g | 0.60 | 0.67 | — |
| Alpha Value | 600 | 3000 | 800 |

*before steaming

EXAMPLE 2

The molecular sieves of Example 1 were each composited with binder alumina and made into extrudates such that each catalyst comprised 65 wt. % of its Molecular Sieve component and 35 wt. % alumina. Extrudate containing Molecular Sieve B was steamed as set out in Example 1.

Each catalyst was then evaluated for transalkylation in identical reactors and at identical reaction conditions. The reactors were ⅜-inch o.d. stainless steel and the reaction conditions were 0 psig, 5 $hr^{-1}$ weight hourly space velocity (based on molecular sieve) and a hydrogen/hydrocarbon mole ratio of 0. Feedstock was 29.6% diethylbenzene, 50.7% benzene 9.1% n-propylbenzene.

Liquid and gas products from the reactions were analyzed by conventional chromatography. Selectivity is defined as weight percent gain of ethylbenzene divided by weight percent losses of diethylbenzene and benzene. Run data are presented in Table III below.

It will be appreciated that the operating conditions for the reaction in accordance with the process of this invention, as exemplified in the foregoing examples, may be varied within the limits specified so that the process may be conducted in vapor-phase, and that various modifications and alterations may be made in the process without departing from the spirit and scope thereof.

TABLE III

| Molecular Sieve | DEB Wt % Loss | Bz Wt % Loss | EB Wt % Gain | Selectivity | (Catalyst) |
|---|---|---|---|---|---|
| A | 13.1 | 5.7 | 25.1 | 134 | 600 |
| B | 12.9 | 9.4 | 30.7 | 138 | 3000 |
| C | 5.9 | 12.2 | 22.2 | 123 | 200 |

Transalkylation
600° F., WHSV 5 — Selectivity $= \dfrac{\text{EB wt \% gain}}{\text{DEB wt \% loss + BZ wt \% loss}} \times 100$

What is claimed is:

1. A process for transalkylating benzene to produce monoalkylaromatics and polyalkylaromatics and recovering monoalkylaromatics, which process exhibits a selectivity for polyalkylaromatic production, the improvement comprising decreasing said selectivity,
   by contacting a feedstock consisting essentially of 40 to 80 wt % benzene, 15 to 50 wt. % dialkylbenzene, and 2 to 20 wt. % $C_9$ monoalkylaromatics and 0 to 5 wt. % $C_9$+aromatics,
   with a catalyst comprising ZSM-5, wherein said ZSM-5 has a silica:alumina mole ratio of from about 20 to about 30 and an alpha value of at least about 140;
   undertaking said contacting at a temperature of from about 400° F. to about 1000° F., a pressure of from about 0 to about 3000 psig, a hydrogen/hydrocarbon mole ratio of from 0 to about 4 and a weight hourly space velocity, based upon weight of active catalyst component, of from about 0.1 $hr^{-1}$ to about 100 $hr^{-1}$; and
   recovering ethylbenzene.

2. The process of claim 1 wherein said zeolite has a silica/alumina mole ratio of from about 20 to about 30.

3. The process of claim 1 wherein said zeolite has an alpha value of about 200 to about 3500.

4. The process of claim 1 wherein said zeolite has an alpha value of about 500 to about 3000.

5. The process of claim 1 wherein said zeolite has the structure of ZSM-5.

6. The process of claim 1 wherein said zeolite contains cations selected from the group consisting of hydrogen and hydrogen precursor.

7. The process of claim 1 wherein said zeolite contains cations selected from the group consisting of hydrogen and hydrogen precursor.

8. The process of claim 1 wherein conditions effective for transalkylation include a temperature of from about 500° to about 850° F., a pressure of from about 25 to about 750 psig, a hydrogen/hydrocarbon mole ratio of from about 0 to 2 and a weight hourly space velocity, based upon weight of active catalyst component, of from about 1 to about 50 $hr^{-1}$.

9. The process of claim 1 wherein said catalyst composition comprises said zeolite and a binder.

10. The process of claim 9 wherein said binder is selected from the group consisting of alumina, zirconia, silica, magnesia, thoria, titania, boria and a combination thereof.

11. The process of claim 10 wherein said binder comprises alumina.

12. The process of claim 1 wherein said catalyst composition is in the form of extrudate, beads, or fluidizable microspheres.

13. The process of claim 1 wherein said zeolite has the structure of ZSM-11.

* * * * *